US00PP19635P2

(12) United States Plant Patent
Miyazaki et al.

(10) Patent No.: US PP19,635 P2
(45) Date of Patent: Jan. 20, 2009

(54) ***ASARINA* PLANT NAMED 'SUNASASHIRO'**

(50) Latin Name: *Asarina*
Varietal Denomination: Sunasashiro

(75) Inventors: Kiyoshi Miyazaki, Shiga (JP); Tomoya Misato, Yamanashi (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 11/998,799

(22) Filed: Nov. 30, 2007

(51) Int. Cl.
*A01H 5/00* (2006.01)

(52) U.S. Cl. ..... Plt./263.1
(58) Field of Classification Search ..... Plt./263.1
See application file for complete search history.

*Primary Examiner*—Annette H Para
*Assistant Examiner*—Georgia Helmer
(74) *Attorney, Agent, or Firm*—C. A. Whealy

(57) ABSTRACT

A new and distinct cultivar of *Asarina* plant named 'Sunasashiro', characterized by its trialing plant habit; vigorous growth habit; freely flowering habit; long flowering period; white-colored flowers; and good garden performance.

1 Drawing Sheet

Botanical designation: *Asarina* hybrid.

Cultivar denomination: 'Sunasashiro'.

BACKGROUND OF THE INVENTION

The present invention relates to a new and distinct cultivar of *Asarina,* botanically known as *Asarina* hybrid and hereinafter referred to by the name 'Sunasashiro'.

The new *Asarina* is a product of a planned breeding program conducted by the Inventors in Higashiomi, Shiga, Japan. The objective of the breeding program is to create new *Asarina* cultivars with attractive foliage and flower coloration.

The new *Asarina* originated from a cross-pollination made by the Inventors in May, 2002 in Higashiomi, Shiga, Japan of a proprietary selection of *Asarina* hybrid identified as code number 3Asa-1, not patented, as the female, or seed, parent with a proprietary selection of *Asarina* hybrid identified as code number 2022-S, not patented, as the male, or pollen, parent. The new *Asarina* was discovered and selected by the Inventors as a single flowering plant within the progeny of the stated cross-pollination in a controlled environment in Higashiomi, Shiga, Japan.

Asexual reproduction of the new *Asarina* by vegetative cuttings in a controlled environment in Higashiomi, Shiga, Japan since 2004, has shown that the unique features of this new *Asarina* are stable and reproduced true to type in successive generations.

SUMMARY OF THE INVENTION

The cultivar Sunasashiro has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Sunasashiro'. These characteristics in combination distinguish 'Sunasashiro' as a new and distinct cultivar of *Asarina:*

1. Trialing plant habit.
2. Vigorous growth habit.

3. Freely flowering habit.
4. Long flowering period.
5. White-colored flowers.
6. Good garden performance.

Plants of the new *Asarina* can be compared to plants of the female parent selection. Plants of the new *Asarina* differ from plants of the female parent selection in the following characteristics:

1. Plants of the new *Asarina* have shorter internodes than plants of the female parent selection.
2. Plants of the new *Asarina* are more freely branching than plants of the female parent selection.

Plants of the new *Asarina* can be compared to plants of the male parent selection. Plants of the new *Asarina* differ from plants of the male parent selection in the following characteristics:

1. Plants of the new *Asarina* have white-colored flowers whereas plants of the male parent selection have red purple-colored flowers.
2. Plants of the new *Asarina* and the male parent selection differ in flower form as plants of the male parent selection have flowers with a closed throat.

Plants of the new Asarina can also be compared to plants of the cultivar Sun-Asaro, disclosed in U.S. Plant Pat. No. 15,532. In side-by-side comparisons conducted in Higashiomi, Shiga, Japan, plants of the new *Asarina* and the cultivar Sun-Asaro differed in the following characteristics:

1. Plants of the new *Asarina* had longer stems and internodes than plants of the cultivar Sun-Asaro.
2. Plants of the new *Asarina* had smaller and less pubescent leaves than plants of the cultivar Sun-Asaro.
3. Plants of the new *Asarina* had smaller flowers than plants of the cultivar Sun-Asaro.
4. Plants of the new *Asarina* and the cultivar Sun-Asaro differed in flower color as plants of the male parent selection had red purple-colored flowers.

BRIEF DESCRIPTION OF THE PHOTOGRAPHS

The accompanying colored photographs illustrate the overall appearance of the new *Asarina,* showing the colors as true as it is reasonably possible to obtain in colored reproductions of this type. Colors in the photographs may differ slightly from the color values cited in the detailed botanical description which accurately describe the colors of the new *Asarina*.

The photograph at the top of the sheet comprises a top perspective view of a typical flowering plant of 'Sunasashiro' grown in a container.

The photograph at the bottom of the sheet is a close-up view of a typical flower and leaves of 'Sunasashiro'.

DETAILED BOTANICAL DESCRIPTION

The aforementioned photographs and following observations, measurements and values describe plants grown in Higashiomi, Shiga, Japan, under commercial practice during the summer in an outdoor nursery day temperatures averaging 23° C. and night temperatures averaging 16° C. Plants had been growing for about four months when the photographs and description were taken. In the following description, color references are made to The Royal Horticultural Society Colour Chart, 2001 Edition, except where general terms of ordinary dictionary significance are used.

Botanical classification: *Asarina* hybrid cultivar Sunasashiro.

Parentage:

*Female, or seed, parent.*—Proprietary selection of *Asarina* hybrid identified as code number 3Asa-1, not patented.

*Male, or pollen, parent.*—Proprietary selection of *Asarina* hybrid identified as code number 2022-S, not patented.

Propagation:

*Type.*—By vegetative cuttings.

*Time to initiate roots.*—About two weeks at temperatures of 20° C. to 25° C.

*Time to produce a rooted young plant.*—About four weeks at temperatures of 20° C. to 25° C.

*Root description.*—Fine, fibrous; pale brown in color.

*Rooting habit.*—Freely branching.

Plant description:

*Plant and growth habit.*—Trailing plant habit. Freely branching with about lateral branches potentially developing at every node. Vigorous growth habit.

Lateral branch description:

*Length.*—About 76 cm.

*Diameter.*—About 2.5 mm.

*Internode length.*—About 4.8 cm.

*Aspect.*—Trailing.

*Texture.*—Sparsely pubescent.

*Color.*—Close to 144B.

Foliage description:

*Arrangement.*—Opposite, simple.

*Length.*—About 5 cm.

*Width.*—About 6.2 cm.

*Shape.*—Ovate.

*Apex.*—Acute.

*Base.*—Cordate.

*Margin.*—Serrate.

*Texture, upper and lower surfaces.*—Sparsely pubescent.

*Venation pattern.*—Pinnate; reticulate.

*Color.*—Developing foliage, upper surface: Close to 144B. Developing foliage, lower surface: Close to 146B. Fully expanded foliage, upper surface: Close to 137C; venation, 145B. Fully expanded foliage, lower surface: Close to 146B; venation, 145B.

*Petiole.*—Length: About 3.9 cm. Diameter: About 1.6 mm. Texture, upper and lower surfaces: Pubescent. Color, upper and lower surfaces: Close to 145B.

Flower description:

*Flower arrangement and habit.*—Single bilabiate flowers arising from leaf axils. Freely flowering habit with numerous flowers developing per plant. Flowers face mostly outwardly. Flowers not fragrant.

*Natural flowering season.*—Plants of the new *Asarina* initiate and develop flowers about four weeks after planting. Long flowering period; flowering commences naturally during the summer and plants flower continuously until late autumn in Japan. Individual flowers last about one week on the plant.

*Flower diameter.*—About 3.1 cm by 3.3 cm.

*Flower length (depth).*—About 6 cm.

*Throat diameter.*—About 1.2 cm.

*Tube diameter, base.*—About 5 mm.

*Tube length.*—About 4.4 cm.

*Flower bud.*—Shape: Globose, elongated. Length: About 5.3 cm. Diameter: About 1.6 cm. Color: Close to 144B.

*Corolla.*—Arrangement: Bilabiate with a two-lobed upper lip and three-lobed lower lip. Length, upper lip: About 1.1 cm. Length, lower lip: About 1.1 cm to 1.2 cm. Width, upper lip: About 1.4 cm. Width, lower lip: About 1 cm to 1.2 cm. Shape, upper lip: Two-lobed; apex, rounded. Shape, lower lip: Three-lobed; apex, rounded. Margin, upper and lower lips: Entire, undulate. Texture, upper and lower lips: Smooth, glabrous. Color, upper and lower lips: When opening, upper and lower surfaces: Close to 149D. Fully opened, upper and lower surfaces: Close to 155C. Color, throat: Close to 149D. Color, tube: Close to 149D.

*Calyx.*—Arrangement: Cup-shaped calyx with five sepals. Sepal length: About 2.5 cm. Sepal width: About 1.1 cm. Sepal shape: Ovate. Sepal apex: Acute. Sepal base: Obtuse. Sepal margin: Entire. Color, upper and lower surfaces: Close to 144B.

*Peduncles.*—Length: About 2.5 cm. Diameter: About 1.5 mm. Strength: Strong. Texture: Smooth, glabrous. Color: Close to 144A.

*Reproductive organs.*—Stamens: Quantity: Four per flower. Stamen length: About 3 cm to 4 cm. Anther shape: Ellipsoidal. Anther size: About 3 mm by 2.5 mm. Anther color: Close to 155B. Pollen amount: Moderate. Pollen color: Close to 155B. Pistils: Quantity: One per flower. Pistil length: About 4.5 cm. Style color: Close to 145D. Stigma shape: Elliptic. Stigma color: Close to 145B. Ovary color: Close to 145C.

*Seed/fruit.*—Seed and fruit development have not been observed on plants of the new *Asarina*.

Garden performance: Plants of the new *Asarina* have been observed to have good garden performance and to tolerate rain, wind and temperatures ranging from about 0° C. to about 35° C.

Pathogen/pest resistance: Plants of the new *Asarina* have not been observed to be resistant to pests and pathogens common to *Asarina*.

It is claimed:

1. A new and distinct *Asarina* plant named 'Sunasashiro' as illustrated and described.

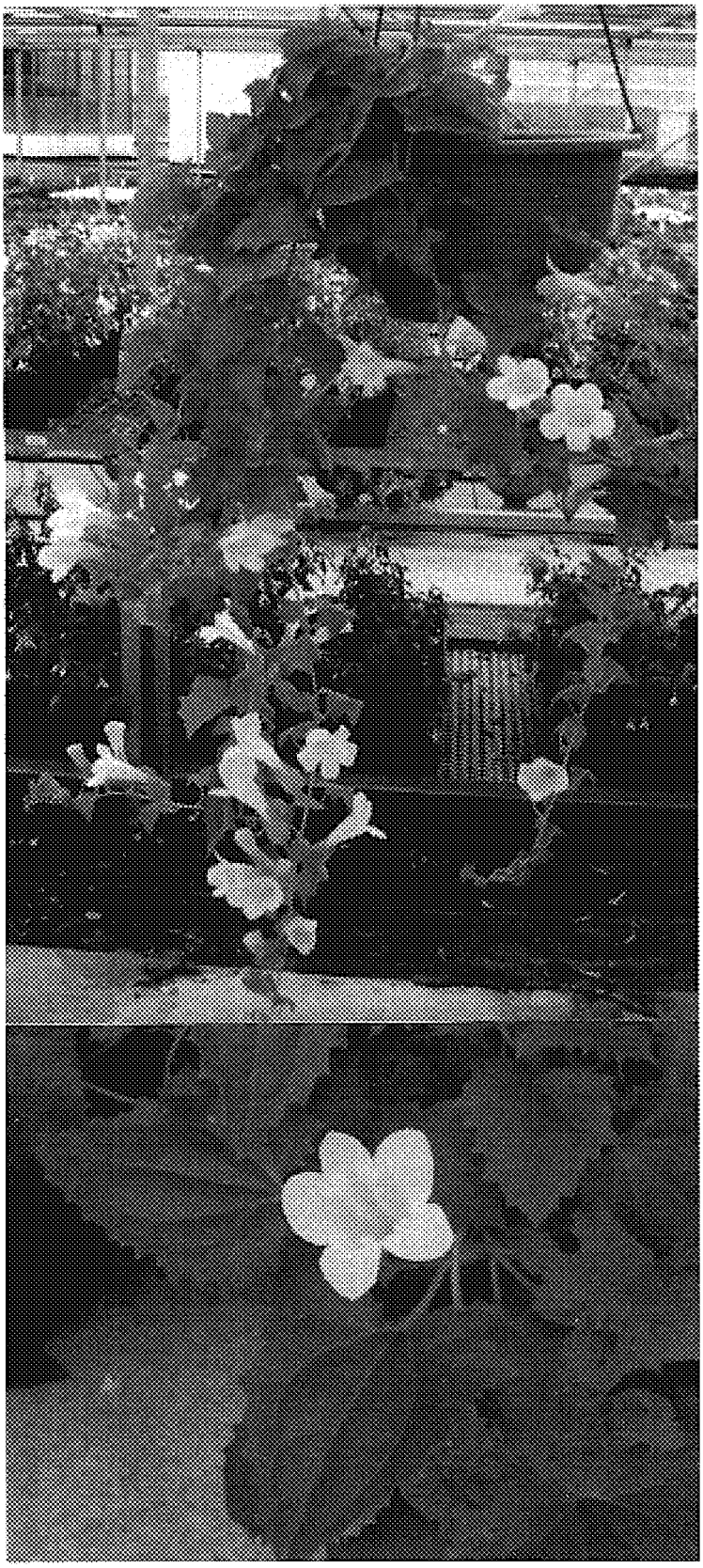

* * * * *